United States Patent
Austrup et al.

(10) Patent No.: US 7,232,653 B1
(45) Date of Patent: Jun. 19, 2007

(54) CANCER CELLS FROM BODY FLUIDS CONTAINING CELLS, ISOLATION THEREOF AND AGENTS CONTAINING THE SAME

(75) Inventors: Frank Austrup, Recklinghausen (DE); Michael Giesing, Berghäuser Strasse 295, D-45659 Recklinghausen (DE)

(73) Assignee: Michael Giesing, Recklinghausen (DE)

( * ) Notice: Subject to any disclaimer, the term of this patent is extended or adjusted under 35 U.S.C. 154(b) by 420 days.

(21) Appl. No.: 09/744,866

(22) PCT Filed: Jul. 27, 1999

(86) PCT No.: PCT/EP99/05386

§ 371 (c)(1),
(2), (4) Date: Apr. 2, 2001

(87) PCT Pub. No.: WO00/06702

PCT Pub. Date: Feb. 10, 2000

(30) Foreign Application Priority Data

Jul. 27, 1998 (DE) ................................ 198 33 738

(51) Int. Cl.
*A01N 1/02* (2006.01)
(52) U.S. Cl. ......................................................... 435/2
(58) Field of Classification Search ............. 435/308.1, 435/261, 2, 378, 398, 399; 436/64, 177, 436/178, 526
See application file for complete search history.

(56) References Cited

U.S. PATENT DOCUMENTS 6,265,229 B1 * 7/2001 Fodstad et al. ............. 436/526

OTHER PUBLICATIONS

Rye PD, et al. Am J Pathol Jan. 1997; 150 (1): 99-106.*
Muller M, et al. Anaesthesist Sep. 1996; 45 (9): 834-8.*
Wagner L, et al. J Endocrinol Mar. 1998; 156: 469-76.*
Ahlqvist J. Acta Cytol Jul.-Aug. 1993; 37 (4): 503-7.*
Van Buskirk RG, et al. In Vitro Cell Dev Biol May 1988; 24(5): 451-6.*
Hirte HW, et al. Gynecol Oncol Mar. 1992; 44 (3): 223-6.*
Kiovuneimi AP. Ann Clin Res Aug. 1976; 8 (4): 272-83.*
Aisenberg AC, et al. J Natl Cancer Inst Jan. 1974; 52 (1): 13-7.*
Allen HJ. et al. Exp Cell biol 1987; 55 (4): 194-208.*
Cobb N. et al. Med Lab Sci Jul. 1990; 47 (3): 172-81.*
Nishiya et al. (Acta Med. Okayama. Apr. 1976; 30 (2): 143-145).*
Sato et al. (GANN Monograph on Cancer Research. 1977; 20: 3-13).*
Khato et al. (Tohoku J. Exp. Med. Jul. 1979; 128 (3): 273-284).*
Rosenthal et al. (Anal. Quant.Cytol. Jul.-Aug. 1979; 1 (2): 84-88).*
Barrett et al. (Acta Cytol. Mar.-Apr. 1976; 20 (2): 174-180).*
Vona et al. (Am. J. Pathol. Jan. 2000; 156 (1): 57-63).*
Zabaglo et al. (Cytometry A. Oct. 2003; 55 (2): 102-108).*

* cited by examiner

*Primary Examiner*—S. Rawlings
(74) *Attorney, Agent, or Firm*—Bacon & Thomas, PLLC

(57) ABSTRACT

The present invention relates to a method for isolating cancer cells from body fluids containing cells. The invention also relates to sets for carrying out said method, cancer cells isolated from body fluids, cell lines established therefrom or derived cell constituents, the use thereof as therapeutic agents or targets, and pharmaceutical or veterinary products containing them. The inventive method is based on the idea that body fluids containing cells are comprised of different sized and different shaped cells and groups of cells. According to the invention, body fluids containing cells or fractions of said body fluids are filtered in a sieve that retains cancer cells. The isolation and characterization of cancer cells is highly important, especially in the field of oncology, in order to respond to questions related to diagnostics, prognoses, therapeutics and scientific matters in human medicine and veterinary medicine. The inventive method also enables cancer cells to be removed totally from fluids or fractions (isolates) thereof containing cells. The isolated cancer cells, cell lines established therefrom and derived cell constituents reflect a substantially native i.e. biological state that can be associated with corresponding cancer cells in a body fluid.

2 Claims, No Drawings

SEQUENCE LISTING

```
<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: PCR primer

<400> SEQUENCE: 1
agggatacta ttcagcccca ggtg                                           24

<210> SEQ ID NO 2
<211> LENGTH: 22
<212> TYPE: DNA
<213> ORGANISM: Artificial Sequence
<220> FEATURE:
<223> OTHER INFORMATION: PCR primer

<400> SEQUENCE: 2
actgccactc cttgccccat tc                                             22

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
gtaagcagga caagatgaca g                                              21

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
gctattctct caggatcttg                                                20
```

```
<210> SEQ ID NO 5
<211> LENGTH: 19
<212> TYPE: DNA
<213> ORGANISM: Artificial Sequence
<220> FEATURE:
<223> OTHER INFORMATION: PCR primer

<400> SEQUENCE: 5
gatgacattt tccctctag                                                19

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
gtggttattg ccttgaaaag                                               20

<210> SEQ ID NO 7
<211> LENGTH: 19
<212> TYPE: DNA
<213> ORGANISM: Artificial Sequence
<220> FEATURE:
<223> OTHER INFORMATION: PCR primer

<400> SEQUENCE: 7
ctcctcccta cttacttgt                                                19

<210> SEQ ID NO 8
<211> LENGTH: 19
<212> TYPE: DNA
<213> ORGANISM: Artificial Sequence
<220> FEATURE:
<223> OTHER INFORMATION: PCR primer

<400> SEQUENCE: 8
aattaacaag gtgtggtgg                                                19

<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
cggatcttct gctgccgtcg                                               20

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
cctctgacgt ccatcatctc                                               20

<210> SEQ ID NO 11
<211> LENGTH: 21
<212> TYPE: DNA
<213> ORGANISM: Artificial Sequence
<220> FEATURE:
<223> OTHER INFORMATION: PCR primer
```

```
<400> SEQUENCE: 11
cgtattcatg ccttgtattt g                                      21

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
cttcttcatc ttcttgttcc                                        20

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
acacaactgt gttcactagc                                        20

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
caacttcatc cacgttcacc                                        20
```

CANCER CELLS FROM BODY FLUIDS CONTAINING CELLS, ISOLATION THEREOF AND AGENTS CONTAINING THE SAME

The present invention relates to a method for isolating cancer cells from cell-containing body fluids; to sets for carrying out said method; to cancer cells isolated from body fluids; to cell lines established therefrom or cell components derived therefrom; to the use thereof as therapeutics or target; and pharmaceuticals or veterinary compositions containing said cancer cells.

The method of the invention is based on cells and cell aggregates of different sizes and shapes being present in a cell-containing body fluid. The isolation and characterization of cancer cells is of great importance, especially in oncology, for solving diagnostic, prognostic, therapeutic and scientific problems both in animal experiments and in human medicine. Moreover, the method of the invention serves to remove, where appropriate completely, cancer cells from cell-containing fluids or cell-containing fractions (isolates) thereof. The isolated cancer cells, cell lines established therefrom and cell components derived therefrom reflect an essentially native, i.e. biological state which can be assigned to corresponding cancer cells in the body fluid.

Isolating cancer cells for carrying out in vitro or ex vivo investigations is unproblematic, for example when a primary tumor has been localized and thus the investigation can be based on a tissue sample. In this sense, U.S. Pat. No. 5,242,806 describes a chemosensitivity test on tumor cells from biopsy material. U.S. Pat. No. 5,023,172 describes the MTS system for testing tumor inactivating active substances which also starts from biopsy material. This material is treated with trypsin and subsequently added to a feeder-cell suspension in order to form multicellular tumor spheroids.

However, problems arise if no tumor has been localized and thus no tissue is available. Although it is known that cancer cells can possibly be detected also in body fluids, appropriate analyses are technically extremely difficult, owing to the low concentration of cancer cells in body fluids. Therefore, traditional medicine in particular often questions the meaningfulness of such analyses.

Thus, isolating cancer cells may be of crucial importance in the context of identifying and characterizing disseminated cancer cells—which include in particular tumorous cells which have detached from the primary tumor, from metastases and/or recurrences and circulate in body fluids. When measuring, for example, the expression of relevant genes by cells of a body fluid to be investigated, then isolation of cancer cells is unnecessary if the non-degenerated cells usually present in the body fluids do not express the relevant genes or express them only to a very small extent. If, however, the non-degenerated cells also express the relevant genes, then it is necessary first to isolate disseminated cancer cells and then to measure the expression of relevant genes. In this case, quantitative analysis of the expression of particular, for example tumor-biologically relevant, nucleic acids (e.g. FAS ligand, FAS receptor, bax, bcl-2, Ki-67, cyclins, adhesion molecules) makes it possible to assign the expression to the tumor isolate.

For the purpose of characterizing the tumor cells, it is sensible to analyze genomic modifications of the tumor cells at the DNA level. Determinations such as "LOH (loss of heterozygocity), mutations, amplifications, etc." need an extremely pure population of tumor cells, since contaminating "wild-type cells" mask potential genomic modifications and thus make them undetectable. The present method removes contaminating, wild-type expressing cells at least to such an extent that genomic modifications of the cancer cells are measurable. Wild-type cells, for example CD45-positive cells, may then serve as references for measuring, for example, LOHs, amplifications and mutations.

Known methods available for isolation purposes frequently lead to a merely nonspecific concentration of cancer cells. Likewise, the leukopheresis method described in U.S. Pat. No. 5,529,903 offers no specific concentration of cancer cells, but provides fractions consisting predominantly of mononuclear cells which can also be obtained using conventional density gradients.

DE 40 062 93 A1 discloses a separating agent made of polyvinyl acetal resin which can remove cells from suspensions. This method is a development of the nylon wool purification of T lymphocytes which has been known for some time. Here too, the basic principle is the preferential adsorption of B cells and macrophages/monocytes to the separating agent.

The method described in the European patent application EP 0 448 837 A2 also concentrates cells from a suspension nonspecifically on a filter, the pressure applied thereto being an indicator for the number of cells.

In order to avoid gynecological smears, EP 0 483 506 A1 suggests filtering menstrual blood. The filter is chosen in such a way that red and white blood cells can pass through the filter pores. The remaining cells which are retained on the filter are then subjected to Papanicolaou staining, and the usual cytodiagnostic evaluation of the cell image is performed in order to distinguish normal from abnormal cells.

The method described in U.S. Pat. No. 5,578,459 serves to collect and concentrate cells quickly from large amounts of liquid such as mouth rinsings. A fractionation of cell mixtures is not taught. Likewise, according to the method described in the Japanese application JP-5-252996A all cells from a solution are to be collected on a filter. This is also the case for the method described in JP-07143898A.

On the other hand, a known possibility for isolating disseminated cancer cells is to use methods in which the cancer cells are labeled in such a way that they are distinguishable from non-degenerated cells and owing to this can be sorted out. Aside from the conventional column technique, for example so-called "cross-flow" and "through-flow" filters loaded with specific ligands are also described for this purpose (for example in WO 96/06158, which is, however, not geared to tumor cells).

Methods of this type are predominantly based on antigen-specific immunoadsorption. Antibodies against particular tumor-specific or epithelial cell surface molecules are, for example, provided with fluorescent and in particular magnetic labels. Disadvantageously, in these methods crosslinking of the surface antigens can cause unpredictable effects such as apoptosis, anergy, activation and other changes in the state of the cells. Such effects can drastically change the picture of a subsequent characterization of the isolated cancer cells. Thus for example, the expression profile of a cell may be affected within a few minutes. Understandably, it is impossible in such cases to rule out that the analysis data obtained in this way reflect apparent properties which the disseminated cancer cells in the body fluid did not have prior to their isolation. However, this would be desirable. As a further disadvantage, the adhering antibodies can be removed only with unfavorable consequences for the cell or not at all. If the antibodies are directed against intracellular components, even fixation and perforation of the cell are necessary, resulting in cell death. In those circumstances, bioassays involving living and, in particular, proliferative cells are very difficult or even impossible. A further disadvantage of purification via antibodies is cross-reactivity of particular epitopes, so that "normal" cells may also be isolated. In addition, cluster formation with blood components, for example platelets, fibria and the like, may obscure epitopes important in the isolation procedure at least partially, so that isolating such cells.

The demands which have to be made on a method for isolating cancer cells in the context of identifying and characterizing disseminated cancer cells are high. In the present case, the authenticity of the isolated cancer cells in particular determines the usability of such an isolation method, aside from the high yield and purity usually required with respect to the product. The cancer cells ought to be isolated from the body fluid essentially unaltered, i.e. not attached to constructs due to the isolation procedure, such as glass beads. They should be culturable ex vivo and represent in bioassays a faithful image of their original state in the body fluid.

A method which fulfills these demands makes use of the crucial advantages which result from identifying and especially characterizing cancer cells from body fluids. When comparing cells from primary tumor tissue with corresponding disseminated tumor cells, the disseminated tumor cells generally have genetic and physiological characteristics different from those of the primary tumor, for example they may be derived from the latter by clonal selection. These characteristics provide important and, where appropriate, additional information for diagnosis, prognosis, prediction and other oncological questions.

It was therefore an object of the present invention to provide a mild method for isolating cancer cells from cell-containing body fluids which has no or only a negligible effect on the state of said cancer cells.

Surprisingly, we found that cancer cells are successfully isolated from cell-containing body fluids by a size- and/or shape-dependent separation process.

The present invention therefore relates to a method for isolating cancer cells from cell-containing body fluids, which is characterized in that the cell-containing body fluid or parts thereof are passed through a screen which retains cancer cells.

Isolating means according to the invention any concentration of a component to be isolated, from a mixture which comprises said component aside from at least one other component. Thus, the isolation may indeed also result in a further mixture which, however, comprises the component to be isolated in a higher concentration relative to at least one other component, compared to the original mixture.

According to the invention, the term cancer cell means a cell which has one or more modifications related to cancer, i.e. degeneration in the general sense. This definition is based on the idea that the development of cancer is a continuous modification process. In general, for example, a plurality of modifications, in particular of the genetic material and/or the expression of the genetic material of cells, are needed on the path from a normal cell to a cancer cell, and in particular to a tumor cell. The term cancer cell therefore also comprises precursors of cancer cells and in particular of tumor cells having cancerous or tumorous modifications. Disseminated tumor cells, i.e. cells which have detached from the primary tumor and circulate in body fluids, are not considered as actual tumor in the medical sense, but they represent cancer cells in accordance with the invention. According to the invention, disseminated cancer cells also include micrometastasized and metastasizing tumor cells, as long as said tumor cells are present in a body fluid of the invention.

A screen according to the invention means a material which facilitates a separation process dependent on size and/or shape, i.e. based on cell size, flexibility, aggregate formation or cluster formation. With respect to the isolation of cancer cells, a screen thus means a separating means which can separate cancer cells from non-cancer cells. The screening process spatially separates cancer cells and non-cancer cells; forms at least two cell fractions; preferably assigns cancer cells to at least one cell fraction and preferably assigns non-cancer cells to at least one further cell fraction; assigns, where appropriate, cancer cells essentially exclusively to at least one cell fraction.

In general, the screen residue contains—depending on cancer cell content of the body fluid—up to 100 cancer cells per ml of body fluid. Compared to non-cancer cells present in the body fluid—in particular to mononuclear cells in the case of blood—concentration factors are achieved of $10^5$ and higher, preferably of at least $5\times10^5$, more preferably of at least $10^6$ and in particular of at least $5\times10^6$. Further separation processes preceding and/or following the screening process can increase said factors. Thus, removing the MNC fraction, for example by density gradient centrifugation, which is usually the first step carried out for blood, achieves concentration factors of about $10^2$.

With a view to the subsequent use of the cancer cells, different demands may be made on the ratio of cancer cells to non-cancer cells. Sensitive investigation methods such as p53 analysis require, for example, a ratio of at least one cancer cell to 1 000 non-cancer cells, while less sensitive investigation methods, such as LOH analysis, require a ratio of at least 1:1.

According to the invention, it is possible to choose a screen through which non-cancer cells of the cell-containing body fluid can just about pass. Likewise suitable is a screen through which also particles larger than non-cancer cells can pass, but which retains the cancer cells or at least some of the cancer cells. Considering a size- and/or shape-dependent separation process, the choice of screen can be optimized, in particular depending on the body fluid used.

In general, the screen is a flat object having openings which are also called meshes. Aside from flat materials, are also suitable porous objects, for example filters, or membrane-like materials. However, an adequate definition of the pore size is required.

The sizes of the screen openings are in general within a particular range. Giving upper and lower limits does not mean that openings with exactly said limits have to be present in the screen. This kind of information means however, that openings whose size is outside the range are not present in the screen. Preferably the size of the screen openings is within a narrowly defined range. Ideally, it is essentially uniform. The size of the screen openings is in the following denoted as mesh width or pore size/pore width.

A screen usable according to the invention has in general a mesh width or pore width of from 10, in particular from 15, to 200 μm, preferably of from 15, in particular from 17, to 30 μm and particularly preferably of about 20 μm. Screens are both screens whose mesh or pore width has a certain distribution within the abovementioned ranges and screens having an essentially uniform mesh or pore width which is within the abovementioned ranges.

Screens having a regular mesh or pore width allow statements about the absolute retention capacity, i.e. the size of the particles which can just about pass through. Screens having an irregular pore or mesh width on the other hand merely permit statement of nominal retention capacities, according to which 98% of all particles larger than said nominal retention capacity are retained.

Screens usable according to the invention have in general an absolute or nominal retention capacity of from 10, in particular from 15, to 200 µm, preferably from 15, in particular from 17, to 30 µm and particularly preferably about 20 µm.

The choice of material for the inventive screens comprising both flat objects, such as screen filters or membrane filters, and porous objects such as depth-type filters is of secondary importance. Mention must be made especially of fiber-forming materials, in particular organic polymers or inorganic fibers, and of agents forming microporous matrices of organic or inorganic origin. Usable examples are resins, gels, granules, sinterable materials, glasses, ceramics, molecular sieves, for example zeolites, etc. Organic polymers may be of natural, i.e. animal or plant origin or may be semisynthetic or fully synthetic. Examples which may be mentioned are keratin-containing structures, hairs, for example camel hair, wool, angora, silk, cellulose-containing structures, cotton, flax, hemp, jute, etc. Semisynthetic polymers based on cellulose, for example cellulose esters, in particular cellulose acetate and nitrocellulose, and also mixed cellulose esters are worth mentioning. Usable fully synthetic polymers include polyolefins, such as polyethylene (PE), polypropylene (PP), cyclopoly-olefins, polyamides, such as nylon (GRILON, GRILAMID), Nylon 6 Nylon 6,6, Nylon 11, Nylon 12, copolyamides (GRILON C), aramids, poly(p-phenylene terephthalamide) (KEVLAR), polyesters, such as poly(alkylene terephthalate), in particular poly(ethylene terephthalate) (PETP), acrylic polymers, such as polyacrylonitrile (DRALON), and acrylates, vinyl polymers, such as poly(vinyl chloride) (PVC), poly(vinyl alcohols), polyester ethers, such as polyether ether ketone (PEEK), polyurethanes, epoxides, fluorocarbon polymers, such as poly(vinylidene fluoride), (PVDF), poly(tetrafluoroethylene) (PTFE, TEFLON), polyhexafluoroethylene/propylene copolymer (FEP), polyethylene/tetrafluoroethylene copolymer (ETFE, AFLON), polyethylene/chlorotrifluoroethylene copolymer (ECTFE, HALAR), polycarbonates, such as PCTE, polyphenylene sulfide (PPS), polyethersulfones, etc. Examples of inorganic fiber-forming agents which may be mentioned are glasses, in particular borosilicates and silicon dioxide, silicon, metals, ceramics, carbon and asbestos. Mixtures of the abovementioned materials may also be used. If required, the materials, in particular the fibers which they constitute, may be modified, for example metallized, hydrophobicized, hydrophilicized, for example with polyvinylpyrrolidone provided with supporting structures, crosslinked or embedded in binders, for example acrylates or melamine resins.

Screens made of solvent-resistant material are advantageous for particular embodiments of the invention. Preference is given to solvent-resistant plastics, such as polypropylene, polytetrafluoro-ethylene, highly fluorinated polymers, vinylidene fluoride, aminoplastics, in particular polyethylene. Metals, glasses and other mineral materials and also particular natural fibers are in principle also suitable.

The production of such screens is within the expertise of the skilled worker; it is possible, for example, to use weaving processes, etching processes, both dry and wet-chemical, laser structuring, e.g. RMPD-mask technology, photolithographic processes, LIGA, etc.

Fiber-forming materials may have different fiber structures. Examples which may be mentioned are smooth, edged, wavy, frayed, fibrous and similar surface forms; circular, elliptical, bone-shaped, dentate, lobate and similar cross-sectional forms; straight-lined, curved, helical and similar axial forms (texture); in the case of more than one component different cross-section distributions, for example in bicomponent fibers arrangements of the two components side by side, as cladding, coating, core-shell type or multiple core arrangements ("islands-in-a-sea").

The weaves are preferably made of threads, fibers, filaments or bundles thereof having openings of very variable geometry. Mono- and/or multifilamentous fibers can be used. Possible woven structures are known not least from the textile sector. Advantageous woven structures are those in which the percentage of the open area (total area of all openings) facilitates a problem-free screening process. Preference is given in general to 1:1 and 2:1 structures. For the surface area of threads, fibers, filaments or bundles, different designs are possible as well. Thus the surface area may be regular or irregular, for example smooth, edged, wavy, frayed or hairy. Further suitable are perforated plates which can also have openings of very different geometry and arrangement.

The screen may be mono- or multilayered. In particular embodiments of the invention, preference is given to monolayered screens. It is also possible to arrange in series a plurality of, where appropriate different, screens.

The screen is expediently arranged in a device which permits passage of the cell-containing liquid through the screen and collection of the flow-through. It should also be possible to remove the screen from said device in order to be able to subject it together with the screen residue to further process steps. If required, means for applying pressures above or below atmospheric pressure may also be provided in order to make the screening process easier. If a preliminary work-up of the cell-containing body fluid precedes the screening process, it may be expedient to link devices and means for carrying out the screening process to devices and means for carrying out the work-up, with the screening process following the work-up. Moreover, the skilled worker may provide for further measures in order to suffice the demands usually made in biochemistry and molecular biology, such as temperature and sterility.

The method of the invention may be applied to all those cell-containing body fluids which have cancer cells and in particular disseminated and micrometastasized cancer cells. These are both native body fluids which are taken from or excreted by the body and non-native liquids, in particular wash liquids, which contain cells from the body and in particular from particular body parts and organs. It is possible, for example, first to administer the liquid to the body in a suitable manner and then to remove it again. Native liquids may also be in a mixture with non-native ones. Examples which may be mentioned are lymph, urine, sputum, ascites, effusions, amniotic fluid, aspirates, wash liquids from organs, for example colon lavage, lung lavage, bronchial lavage or bladder irrigation fluid, feces, and in particular bone marrow and blood. The body fluids may be from different species, for example from mammals, in particular humans, laboratory animals and experimental animals such as mice, rats, rabbits, guinea pigs, etc. Such body fluids may be directly fed to the screening process. However, frequently it is advantageous to subject the cell-containing body fluid to a preliminary work-up first. It is possible, for example, to separate cellular from non-cellular components. Likewise, the cellular components, where appropriate, can be further fractionated, for example by isolating a cell-containing fraction which is known also to include cancer cells. For this purpose, the physical separation methods described at the beginning, such as density gradient centrifugation, are particularly suitable.

When isolating cancer cells from blood, it is preferable according to the invention first to remove white blood cells by density gradient centrifugation. Cancer cells are found especially in the fraction containing mononuclear cells, so that this is the preferred fraction to be used in the subsequent screening process.

Furthermore it is also possible to modify the cancer cells in the cell suspension prior to the screening process, for example by labeling, by attaching particles, by triggering aggregation and/or cluster formation using, for example, suitable antibodies, enzymes, lectins, other ligands and/or receptors or crosslinking reagents, by fixing and by inducing other defined states.

In order to be able to be fed to the screening process, the cell-containing fractions (isolates) isolated beforehand from a body fluid should be present in the form of suspensions. The suspension medium of choice is preferably a buffer or a culture medium. The suspension medium should have no effect on the cell properties of interest, if possible.

Before the cell-containing body fluid or isolates thereof are passed through a screen, it is advantageous for later evaluation to remove aliquots of cell-containing liquid. Such samples may serve as references for data obtained from screen residue and flow-through. This facilitates comparison with non-cancer cells, for example lymphocytes isolated as CD45-positive cells as a patient-specific internal control, and this in turn makes particularly sensitive analyses of the isolated cancer cells possible.

The screening process has finished when the entire cell-containing liquid has passed through the screen. A washing process may follow, in which further liquid, preferably buffer or culture medium, is passed through the screen. The wash liquid may be combined with the flow-through obtained beforehand or else be collected separately thereof and, where appropriate, discarded.

The cell fraction retained on the screen may be directly put to its subsequent use, for example to characterizing the cells, in particular the cancer cells, or stored. It is advantageous, however, first to remove the cells, in particular the cancer cells, from the screen. Depending on the subsequent use, it is possible to choose different procedures for this purpose.

One possibility is to wash off the cells, in particular the cancer cells, retained on the screen by passing a suitable liquid through the screen in the opposite direction and obtaining the cell-containing wash liquid. The removed cells may then he pelleted from the cell suspension, if desired.

It is also possible to remove the cells, in particular the cancer cells, attached to the screen by the use of force. Gravity, centrifugal force and electrical forces may be employed. Sedimentation, centrifugation, electrophoresis, dielectrophoresis, the use of so-called optical tweezers, electroosmosis, and similar methods are familiar to the skilled worker for this purpose. This works, for example, by introducing the screen into a suitable medium, usually a liquid, in such a way that the cells can be pelleted by centrifugation. In this way it is possible to transfer the cells directly into a medium suitable for the subsequent use.

Another possibility which likewise removes the cells, in particular the cancer cells, from the screen but which at the same time destroys said cells, is to introduce the screen complete with attached cells into the methods used for obtaining cell components, for example nucleic acids and proteins. If such measures require the use of organic solvents, for example when using solutions which contain guanidine isothiocyanate and phenol and which are frequently used in this area for isolating total RNA, DNA and proteins, then screens made of solvent-resistant materials are preferred.

The method of the invention isolates cancer cells from cell-containing body fluids. Isolating cancer cells in accordance with the invention means preparing cancer cell-containing cell mixtures from body fluids, the ratio of cancer cells to non-cancer cells being greater in the prepared cell mixtures than in the original cell-containing body fluids. Thus isolating means concentrating cancer cells in cell-containing fractions of body fluids. Cell containing fractions having an increased cancer cell content are prepared and obtained.

The cell-containing fractions are preferably cell mixtures having a cancer cell content of at least 50%, more preferably of at least 80% and in particular of at least 90%.

Isolating in accordance with the invention also means obtaining cancer cells which are essentially free of non-cancer cells. Said cancer cells may be obtained in the form of cancer cell mixtures which are in general polyclonal but which may also have some characteristics in common. It is however also possible to obtain fractions of said cancer cell mixtures and also individual cells which have (further) characteristics in common and/or, where appropriate, may even be monoclonal. For this, the cancer cells isolated, i.e. concentrated according to the invention from cell-containing body fluids may have to be classified into subtypes on the basis of stratification parameters (e.g. immunologically) and/or further purification. Examples which may be mentioned are laser microdissection, micromanipulation, dielectrophoresis, electroosmosis, optical tweezers, FACS and the like after specific addressing.

Isolating in accordance with the invention also means removing cancer cells from cell-containing preparations, in particular from body fluids or parts thereof, i.e. reducing the cancer cell content in cell-containing preparations, for example from blood or blood components, preferably extracorporeal, from stem cell preparations or other reinfusion, transfusion and transplantation preparations.

Thus, the method of the invention may also be applied to the, where appropriate complete, removal of contaminating cancer cells from cell mixtures, i.e. cell containing preparations, in particular from body fluids or isolates thereof (depletion).

The present invention therefore also relates to methods for removing, in particular for extracorporeally eliminating, cancer cells, in particular tumor cells, from cell-containing preparations, in particular body fluids or parts thereof, and also to methods for depleting stem cell preparations or other reinfusion and/or transfusion preparations for reducing the cancer cell content. The purpose of said methods is, in particular, recurrence prophylaxis. Disseminated tumor cells in body fluids and in other cell preparations represent a considerable risk factor for the development of recurrences and metastases. The concentration and composition of the cells—aside from their genetic disposition—have an influence on the probability of metastasis development. Reducing the concentration of cancer cells, in particular of disseminated tumor cells, in said body fluids by a method which removes said cells extracorporeally reduces the probability of a recurrence. For example, many tumor patients receive autologous cell isolates after radio- and/or chemotherapy. These cells, for example apheresis products, isolated stem cells and the like, can be freed of cancer cells in a mild manner using the method of the invention. In this way it is possible to reduce the recurrence risk from contaminating cancer cells.

The present invention therefore also relates to a method for treating the human or non-human animal body with the therapeutic aim of recurrence prophylaxis.

The present invention also relates to the screen residue obtained according to the invention and also to fractions derived therefrom, if required by using further measures known per se, in particular to cell mixtures, cancer cell mixtures, cancer cell clones and/or cancer cell components. Thus, the invention also relates to cell mixtures, cancer cell mixtures, cancer cell clones, cell lines established therefrom and/or cancer cell components, all of which are obtainable from body fluids using one of the methods described above and are collectively designated cancer cell material.

Preference is given to cell mixtures derived from body fluids and having a cancer cell content of at least 50%, preferably of at least 80% and in particular of at least 90%. The remaining content may in each case be non-cancer cells from the relevant body fluid.

Particular preference is given to cancer cell mixtures which are derived from body fluids and which contain only small amounts of and preferably no non-cancer cells. Said mixtures are in general polyclonal. Although polyclonal, they may nevertheless be homogeneous in relation to at least one characteristic, for example a particular genomic disposition or an expression parameter. Preference is given to cancer cell mixtures which are essentially homogeneous with respect to at least 1, 2, 3, 4, 5, 10 or 15 parameters which are to be analytically determined. These determinations include cancer-detecting analyses, tumor-biologically relevant analyses for measuring cytophysiological parameters, analyses of pharmacologically relevant parameters, bioassays, cytological analyses, and similar methods, which in the following are discussed in more detail.

Particular preference is given to cancer cell clones, i.e. individual cancer cells or monoclonal cancer cell lines.

Cell lines may be established starting from the above-described cell mixtures, cancer cell mixtures and cancer cell clones, especially from cancer cell mixtures and in particular from cancer cell clones. The cell lines can be both short-term and long-term. The relevant skilled worker is able to establish said cell lines in an appropriate manner and is familiar with suitable methods, for example in view of choosing culture medium or culture conditions and also storage and preservation. Where appropriate, it is possible to refer back to information on already established cancer cell lines such as HeLa.

Cell components derived from the above-described cell-containing preparations include, for example, cell lysates and also fractions thereof, i.e. particular cell components such as nucleic acids, proteins, etc., which can be isolated in an appropriate manner by the skilled worker from the cell-containing preparations obtained beforehand.

According to the invention, cancer cells are successfully provided which have been isolated from body fluids and which are free from the separating agent used. Thus, they are in particular free of ligands conventionally used for isolation purposes, such as antibodies, lectins, etc. The cancer cells of the invention are therefore in a biological state and not in an artificial state which is usually brought about during their isolation, for example by fixing and/or labeling. A biological state in accordance with the invention is therefore a state which the relevant cell may adopt in a body fluid of a human or non-human animal individual, in particular in relation to physiology, morphology and/or expression profile. Important for describing said biological state are especially parameters relating to the cell cycle, activation, proliferation, apoptosis and the like. Said parameters are left essentially unchanged by the isolating process of the invention. A biological state may thus be characterized by one or more of the following properties mentioned by way of example: vital, capable of division, proliferative, culturable, preapoptotic, apoptotic, dead, isolated, aggregated, cluster-forming, etc.

The present invention therefore also relates to cancer cells, in particular disseminated tumor cells, which have been isolated from body fluids—and are likewise to be classified under the inventive term cancer cell material—and which are in a biological, preferably vital state, where appropriate in a mixture with non-cancer cells, and to cell lines established therefrom. Isolated in this connection means that the ratio of cancer cells to non-cancer cells is greater than in the original body fluid. Preference is given to a cancer cell content of at least 50%, preferably of at least 80% and in particular of at least 90%. Very particularly preferred are essentially pure cancer cells which in an advantageous embodiment have the characteristics of the above-described cancer cell mixtures, cancer cell clones and cell lines established therefrom.

Cancer cells of the invention which are characterized by a quantitatively and/or qualitatively particular combination of parameters (pattern) form a particular aspect of the present invention. The pattern-forming parameters relate especially to genomic dispositions and/or expression profiles. Particular cancer cells result for example with reference to the combinations of particular genes, as disclosed in WO 99/10528, for carrying out multiparameter expression analyses and also genomic tests for oncogenes and/or mutated tumor suppressor genes. Examples which may be mentioned, therefore, are cancer cells expressing CEA and CK20, where appropriate in combination with tumor-specific splice variants of the MUC1 gene; or expressing MAGE3 and tyrosinase, where appropriate in combination with Mucl8; and/or cancer cells having at least two of the genomic dispositions selected from p53 mutations and/or p53 LOHs, erb-B2 amplifications, c-myc amplifications and K-ras mutations, where appropriate in combination with LOHs of the genes RB, APC, DCC and/or DPC4; and/or cancer cells expressing maspin and/or progesterone receptor, where appropriate in combination with β-hcG, estrogen receptor and/or SCCA; expressing PSM and/or PSA, where appropriate in combination with hK2; expressing gastrin, where appropriate in combination with GIP and/or motilin; or expressing SP-A and SP-C, where appropriate in combination with β-hCG; and/or expressing bFGF, bFGF-R, VEGF-R1 and/or VEGF-R2, where appropriate in combination with VEGF; expressing MMPs, in particular MMP2; and/or expressing TIMPs, in particular TIMP3; and/or expressing FAS-L and FAS-R; expressing, where appropriate, cyclins, in particular cyclin B, D and E in cell-cycle-specific ratios, Ki67, bax and/or bcl-2. Expression can mean qualitative expression and also expression which is quantitatively increased or reduced compared to non-cancer cells. The patterns described above may also characterize cell lines established from the cancer cells and derived cell components.

It is, of course, possible to subject the isolated cancer cells to specific manipulations which convert the biological state into an artificial state, for example by fixing the cells, labeling the cells, for example radiolabeling using PET labels, NMR probes, etc., or by inducing another state which may even correspond to a biological state.

The present invention therefore also relates to cancer cells, in particular disseminated tumor cells, which have been isolated from body fluids—and are likewise to be classified under the inventive term cancer cell material—and which are in an artificial state induced after isolation and starting from a biological state, where appropriate in a mixture with non-cancer cells, and also to cell lines established therefrom. Preferred embodiments of this subject of the invention arise analogously to the above described embodiments of cancer cells of the invention having a biological state.

Likewise, components of the cancer cells of the invention, for example lysates or fractions thereof, are characterized in their structure and/or composition by the fact that they are derived from the cell components of the invention.

The present invention therefore also relates to cell components—likewise to be classified under the inventive term cancer cell material—which have been derived from inventive cancer cells with biological or induced artificial state. Said cell components may be prepared from the appropriate cells in a manner known per se.

The cancer cell material of the invention may be compiled in the form of substance libraries, for example cell libraries or biorepositories. An expedient storage is within the expertise of the skilled worker, taking into account the material to be stored. Cryo-storage, for example in nitrogen, is particularly suitable for living and/or sensitive material. It is possible to prepare the cancer cell material in this form for commercial utilization with a view to further uses. Cell components on the other hand, may possibly be traded as chemicals—also at relatively high temperatures, where appropriate cooled by dry ice or ice, or even at room temperature in suitable packaging, depending on the sensitivity.

The present invention further relates to compositions, for example pharmaceuticals or veterinary compositions for diagnostically and/or therapeutically treating humans or non-human animal creatures, which compositions comprise cancer cell material of the invention—aside from further useful components to be selected by the skilled worker, in particular formulation excipients for administration, and further active substances and/or components of a diagnostic test. These compositions thus comprise cancer cells, in particular disseminated tumor cells, which have been isolated from body fluids and which are in a biological state or artificial state induced after isolating, and/or cell components derived therefrom. Mention may be made here by way of example of applications such as the formulation of autologous or heterologous vaccines in therapy or the establishing of controls in diagnostic test systems.

The present invention also relates to the use of the cancer cell material of the invention as therapeutic agent, i.e. for producing pharmaceuticals and/or veterinary compositions for therapy, or as target in diagnosis, therapy, animal experiments or science.

Thus it is possible to use the cancer cell material of the invention for characterizing particular patterns, in particular genomic dispositions and/or expression profiles. Depending on the underlying pathology, in particular on the type and the course of a cancer, where appropriate taking into account therapeutic measures already carried out, it is possible to provide instructions which are useful for diagnostic and/or therapeutic methods and are directed toward a particular result.

The use as therapeutic agent relates in particular to vital cancer cells and very particularly to the establishment of vaccines. Aside from heterologous immunization which is likewise possible, this is particularly relevant to autologous immunization. For this purpose, the cancer cell material of the invention is, where appropriate, prepared in a suitable manner, so that antibodies and/or immunoreactive cells are generated against the cell surface or against cell components, after injection in the form of an acceptable formulation. Mention may also be made of the use as drug vehicle, i.e. as specific in-vivo transport medium, in particular for therapeutically active substances. In the context of another therapeutic use, the removed cancer cell material is modified first—examples of methods worth mentioning here are those known under the bywords of microinjection, gene transfer, antisense, knockout, etc.—and then readministered to the individual to be treated, for example by reinfusion.

The cancer cell material of the invention is used as a target in diagnosis, therapy, animal experiments and science.

The use in diagnosis relates in particular to characterizing cancer cells from body fluids. Characterizing includes both identifying and detecting the cancer cells as such and determining one or more parameters on those cancer cells. In relation to human or non-human animal individuals, said use relates in particular to the method described in WO 99/10528 for characterizing disseminated and micrometastasized cancer cells on the basis of DNA and/or RNA.

The present invention therefore also relates to a method for characterizing disseminated and micrometastasized or metastasizing cancer cells on the basis of DNA and/or RNA, wherein cancer cells removed from body fluid of an individual using the method of the invention are tested on the basis of DNA and/or mRNA for at least one cancer-specific gene and the same test is performed on non-cancer cells of the same individual for comparison and, where appropriate, cells obtained from body fluid of an individual in a conventional manner, in general cell-containing fractions of the appropriate body fluid, are tested for at least one cancer-specific gene on the basis of mRNA. Particular embodiments and implementations of this method result from referring to the methods disclosed in claims 1 to 10 of WO 99/10528, in particular taking into account the genes mentioned in the glossary and further combinations of particular genes, as disclosed in WO 99/10528, for carrying out multiparameter expression analyses and also genomic tests for oncogenes and/or mutated tumor suppressor genes.

Independent of and also in addition to characterization on the basis of DNA and/or RNA, it is also possible to study on the cancer cell material of the invention proteins, sugars, glycosylation structures, ribozymes and the like, in order to characterize disseminated and micrometastasized or metastasizing cancer cells.

Identifying and characterizing isolated cancer cells in particular includes carrying out cancer-detecting analyses, for example analyses of nucleic acids for mutations, insertions, deletions, LOH, amplifications, aberrations in the chromosome set and the like; tumor-biologically relevant analyses for measuring a great variety of cytophysiological parameters connected with, for example, metastasizing, the cell cycle, proliferation or apoptosis of cancer cells; analyses of pharmacologically relevant parameters, with the isolated cells being cultured in vitro under various conditions, for example with the addition of cytostatics, antagonists and the like, so that various therapy forms can be tested in vitro and optimized individually for each patient; bioassays which may determine activation, inhibition or other modifications of the isolated cancer cells by cytoactive molecules such as cytokines, chemokines, hormones, growth factors, ligands, chemical or biological analogs, apoptosibility of the isolated cancer cells or their apoptotic potential toward other target cells, or else radiation sensitivity of the isolated cancer cells to estimate the individual dose for a patient; cytological analyses using known methods such as immuno-histochemistry, counterstaining, FISH or other cytological detection and staining methods. Mention may be made of the following analyses by way of example:

cancer-detecting DNA/RNA analyses relevant to oncogenes and tumor suppressor genes such as p53, genes of the ras family, erb-B2, c-myc, mdm2, c-fos, DPC4, FAP, nm23, RET, WH1 and the like, and also LOHs for example in relation to p53, DCC, APC, Rb and the like, and also BRCA1 and BRCA2, in hereditary tumors, microsatellite instability of MSH2, MHL1, WT1 and the like, tumorous RNAs such as CEA, cytokeratins, e.g. CK20, MUC1, MAGE3, Mucl8, tyrosinase, PSA, PSM, BA46, mage-1 and the like, or morphogenic RNAs, such as maspin, HCG, GIP, motilin, hTG, SCCA-1, AR, ER, PR various hormones, and the like;

analyses of tumor-biologically relevant RNAs and proteins, which are relevant to the metastasizing profile, i.e. expression of angionesis molecules, motility molecules, adhesion molecules and matrix degradation molecules, such as bFGF, bFGF-R, VEGF, VEGF-Rs such as VEGF-R1 or VEGF-R2, E-cadherin, integrins, selectins, NMPs, TIMPs, SF, SF-R and the like, to the cell cycle profile or proliferation profile, such as cyclins (e.g. the expression ratio of cyclin D, E and B), Ki67, P120, p21, PCNS and the like, or to the apoptosis profile, such as FAS (L+R), TNF (L+R), perforin, granzyme B, BAX, bcl-2, caspase 3 and the like.

An obvious possibility is to carry out such methods in the context of screening processes, inter alia for early tumor diagnosis and/or tumor localization. Further to be mentioned are specific applications, for example detecting a particular carcinoma or a particular mutation, the latter for example in aftercare, e.g. for monitoring the course, in particular in view of a mutation which is the basis from which the tumor has developed. Said specific applications may be advantageously provided as test systems, where appropriate with instructions and further test components such as primers, controls, etc., for example in the form of kits.

Further uses in diagnosis relate to quality control of cell-containing preparations, for example detecting tumor cells in stored blood, in transplantation medicine for checking stem cell preparations and other transplants, where appropriate after removing cancer cells, both in autologous and heterologous preparations which may possibly contain cancer cells even when a solid tumor has not been detected yet. In forensic medicine, it is possible in this way to identify successfully the cause of tumor infections which are mediated by stored blood or other transplant ion products.

The use of the cancer cell material of the invention in therapy relates in particular to therapy development, therapy selection, therapy monitoring and evaluation of possible therapy resistances.

In the context of therapy development, drug targeting may be mentioned as an example, in particular employing the cancer cell material of the invention for identifying novel therapeutic targets, for identifying a further target group for medicaments possibly already approved, in particular evaluating target expression and/or polymorphisms under the influence of particular therapeutics such as, for example, antibodies, ligands and receptors, enzymes, inhibitors, chemotherapeutics, lectins, lipids, catalytic substances, etc., determining effectors such as, for example, signal transduction factors or effects such as, for example, preapoptosis, apoptosis, anergy, further effects relating to the cell cycle, etc., or testing said effectors and effects for modifications by clonal selection, where appropriate before and/or after treatment with particular active substances. Furthermore, the use of the cancer cell material of the invention in the context of therapy development also relates to checking therapeutic targets by ex-vivo studies, for example in cell cultures and on animal models.

In the context of active substance development, the cancer cell material of the invention is applied to screening of active substances, for example for identifying and characterizing lead substances, e.g. vectors, antisense molecules, ribozymes, toxins, chemotherapeutics, antihormones, etc. In general, and especially after high throughput screening (HTS), the drug discovery process results in a plurality of hits or lead substances, and the substances which are continued to be monitored can be further narrowed down in the cancer cell material of the invention ex vivo, in vitro and/or in vivo, for example in an animal model. This may produce a connection to the current tumor situation.

In this connection, mention has to be made in particular of the development of active substances against surface structures of cancer cells. Methods which can generate macromolecules binding to particular structures are known to the skilled worker; specificity and affinity of said macromolecules improve continuously due to self-optimizing processes. Selection processes eliminate unwanted binding properties. By using the cancer cell material of the invention as carrier of the desired structures, it is possible to develop specific therapeutics such as antibodies, aptamers, etc.

The cancer cells of the invention are also applied to secondary screening. In general, the substances identified in the primary screening have still to be optimized, for example in relation to their producibility, the costs of synthesis, stability, kinetic properties, their metabolic behavior, and the like. An important factor is the optimal effect on the therapeutic target. It is possible to carry out this and further optimizing processes advantageously by ex vivo studies using the tumor cells of the invention, since these represent one of the essential therapeutic targets. The use of said cancer cells in active substance development makes it possible, to consider also the cancer cell-specific metabolism, and this is of considerable importance in particular for developing prodrugs. A specific activation in or on the target cell is desirable, for example by removing other components from active substance conjugates, which in this way are converted to an active form only by a cancer cell-specific activity. Another area for the use of the cancer cells of the invention is the development and/or checking of vectors, for example for gene therapy, which can effectively introduce nucleic acids into the cancer cells. By using the cancer cell material of the invention, it is possible to adapt vectors to the target cell structure, in particular to their genetic make-up, and to check ex vivo the effectiveness of the introduction process.

Furthermore, the cancer cell material of the invention is used for determining the therapeutic range of an active substance by comparing in vitro the effects of an active substance on cancer cells and on non-cancer cells. For example, a cytostatic therapy ideally ought to affect exclusively cancer cells. Said application makes it possible to recognize possible side effects.

From the above description, it is immediately evident that it is possible to use the cancer cell material of the invention also for selecting an individually suitable therapy which is not only determined by the type of cancer, but also depends on the particular individual and the state of the disease.

The cancer cells of the invention are also used for therapy monitoring, i.e. the time-dependent evaluation of a therapeutic measure. This application is possible for an existing solid tumor which may have been either diagnosed or else, in an animal, transplanted or induced. The transfer of the cancer cell material of the invention into an animal such as mice, rats and other mammals, hen's eggs, and the like is also possible. It is possible to record kinetics of the time course of the cancer cell concentration in the body fluid studied and of the development of selected cancer cell parameters.

Furthermore, using the cancer cell material of the invention makes it possible to detect possible therapy resistances, for example against chemotherapeutics and other active anti-cancer substances. Both in vitro and ex vivo analysis methods and test systems are suitable here.

The cancer cell material of the invention may also be used for establishing highly specific tumor models, for example for specifically inducing tumors or for evaluating the effects of cancer cell material of the invention on and its behavior in organisms. For this purpose, the cancer cells may be administered, where appropriate in labeled form, to suitable experimental animals, for example by reinfusion.

Furthermore, the cancer cell material of the invention is used for investigating numerous scientific and practical questions, for example for identifying and/or characterizing tumor inducers and tumor enhancers such as, for example, viruses, bacteria, intracellular parasites, alkylating and other mutagenic substances, etc.; for providing novel structures, for example for identifying and isolating novel genes, gene products, proteins, glycosylation structures, etc., inter alia in relation to novel therapeutic targets and/or diagnostic tools; for inducing knockouts and for function studies; for identifying particular expression profiles, for example altered gene expression patterns depending on the tumor-biological state of a cancer cell, inter alia in relation to metastasis, development of resistance before, during and/or after therapy, or compared to cells from normal tissue, primary tumor tissue, recurrence tissue or metastatic tissue; for identifying particular polymorphisms or combinations; for studying the variability of genetic information, for example for identifying structural nucleic acid modifications such as mutations, splice variants, etc.; in proteomics, both analytically and preparatively with possible subsequent applications, for example with the aid of confocal laser scanning microscopy or other methods such as Maldi-Tof, ES-MS/MS; for studying cell—cell interactions, for which the cancer cell material of the invention may be incubated together with manipulated killer cells, for example; for isolating and characterizing cancer cell components both from cultured and from non-cultured cancer cells, for example proteins such as lipoproteins, glycoproteins, etc., peptides, lipids, carbohydrates, etc. On the basis of the cancer cell material of the invention, it is possible to elucidate relations of origination, development and effect of therapies, and, building on this, novel therapies are provided, especially in relation to the rationale for therapy combinations.

If identifying and characterizing the isolated cancer cells requires a prior isolation of nucleic acids, proteins or other cell components, then a multiplicity of various methods is known to the skilled worker which he can use for managing said isolation. Only a few methods may be pointed out here by way of example.

To isolate genomic DNA, it is possible to lyze the cells, for example through the action of detergents and/or proteinases, to remove the proteins and to isolate the DNA, for example by precipitation using known organic solvents. Methods based on solutions containing guanidine isothiocyanate and phenol are preferred. Chromatographic purification, i.e. separation of nucleic acids and other cell components and/or separation of different types of nucleic acid, for example by means of extraction on solid phases such as silicates and the like, e.g. using commercial spin columns, may also be worthwhile. Other known methods, such as techniques involving probes, electrophoresis, electroosmosis and osmotic shock, may be expedient. Similar methods are used for isolating total RNA. From this total RNA, mRNA may in turn be isolated by using system based on oligo(dT), for example. The choice of an expedient protocol is subject to the knowledge of the skilled worker.

It is then possible to use the isolated nucleic acids for further identification and characterization in a multiplicity of applications. These include, for example, PCR, RT-PCR, DD-RT-PCR, cDNA synthesis, primer extension, digestion by restriction enzymes, Southern blotting, labeling reactions and modification reactions, Northern blotting, cloning, sequencing, in vitro transcription or in vitro translation. It is also possible to carry out some of the above-mentioned applications on one or a few cells without prior isolation of nucleic acids, in particular RT-PCR. The choice of a suitable application depends not only on the type of nucleic acid, but also on the genetic information on the basis of which the cancer cells are to be identified and characterized.

High purity of the isolated cancer cells and preservation by the isolation technique of their original state are particularly advantageous results of the invention. This makes it possible to carry out particular functional tests, for example in relation to pharmacogenomics (test with particular active substances) or of modifications of the isolated tumor cells (gene therapy, gene replacement). Moreover, the purity of the cells makes it possible to carry out so-called drug targeting. Thus, for example, a detected erb-B2 amplification suggests a therapy with anti-erb-B2 antibodies or other ligands; tumor cells expressing progesterone receptor or estrogen receptor are accessible to so-called anti-hormone therapy. If, for example, a mutation of the β-tubulin gene is detected in the cancer cells, this would be a contraindication of Taxol®. The same is true in relation to Tamoxifen® for detecting particular splice variants of the estrogen receptor.

The present invention further relates to sets for isolating and, where appropriate, subsequently identifying and characterizing disseminated and metastasized cancer cells. The invention also relates to sets for depleting cancer cells from cell-containing preparations, in particular from body fluids or isolates. Such sets should be very simple to operate and essentially be ready to use. A preferred arrangement makes the sets available in the form of kits. The essential component of suitable sets is at least one screen of the invention. In accordance with the 'ready to use' concept, said screen may have already been adapted according to the use, or else has been added to the set as a kind of raw material which the user may adapt according to particular demands, for example it may be cut to fit particular labware. In addition, components may be present which make it possible to pass cell-containing body fluid or parts thereof through the screen, for example column-like parts in which the screen is expediently arranged and from which it can also be removed again;

to collect the screen flow-through;

to remove cells or cell components from the screen and/or to take them up, for example solutions such as buffers, culture media or organic solvents and/or solvent mixtures such as ethanol, chloroform, isoamyl alcohol, isopropanol, guanidine isothiocyanate, phenol and mixtures thereof, e.g. Trizol®, preferably as ready-to-use solutions or solvent mixtures which may be available in containers which can preferably be centrifuged, and also separately from these;

to isolate nucleic acids, proteins or other components of the isolated cancer cells or at least to prepare said molecules for an, with a view to subsequent analyses, expedient isolation, for example the abovementioned solutions, spin columns with suitable solid phases, oligo(dT) systems, and the like.

Sets of this type can be employed universally and are substantially independent of the type of possible preliminary work-up of the cell-containing body fluid and of the subsequent uses, for example of the analyses to be carried out for identifying and characterizing isolated cancer cells.

Furthermore, components may be present which make it possible to carry out preliminary work-up of the cell-containing body fluid, for example for isolating cells or particular cell-containing fractions from said body fluid;

to carry out the intended analyses for identifying and characterizing isolated cancer cells, in particular studies of the genes and proteins mentioned above, for example primers, means for amplification, detection and/or controls. The controls may also be cancer material of the invention;

Owing to the great variety of such measures, said components are in general included in the set of the invention only to a limited extent, if at all, i.e. each set is geared to a particular body fluid and/or to one or a few analyses. The kits in this case are kits for carrying out an identification and characterization of isolated cancer cells on the basis of one or a few parameters.

The following examples are intended to illustrate the invention in more detail without restricting it.

EXAMPLE 1

Isolating Disseminated Cancer Cells from Blood 10 ml of heparinized blood are centrifuged (400 g; 10 min; RT). The plasma supernatant is removed. The pelleted cells are suspended in 12 ml of PBS. After density gradient centrifugation (Nycodenz 1.077; 800 g; 30 min, RT), the interphase cells (mononuclear cells, MNC for short) are removed and washed in 2×10 ml of PBS (1 mM EDTA) (400 g; 10 min; 4° C.). The MNCs are suspended in 10 ml of PBS (1 mM EDTA, 0.5% BSA). 1 ml of this cell mixture is removed as reference (control fraction). The remaining 9 ml of cell mixture are passed via a column through a 20 µm mesh screen woven from PE threads (sold by SEFAR AG, Rüschlikon, Switzerland) and the flow-through is collected. The column is washed 5× with 10 ml of PBS (1 mM EDTA) each. The screen is removed, turned over and incubated with 0.7 ml of Trizol® (5 min; RT) in a reaction vessel. The screen is placed in the reaction vessel above the Trizol® solution and centrifuged (200 g; 30 s; RT). The dry screen is removed and the Trizol® solution is used for further RNA/DNA isolation.

As an alternative to incubating the screen in Trizol®, the screen may be removed from the column, turned over and transferred into PBS (1 mM EDTA, 0.5% BSA), and the cells may be pelleted by centrifugation (400 g; 10 min, 4° C.).

EXAMPLE 2

Isolating CD45 Positive Cells (Control Fraction)

To isolate CD45 positive lymphocytes as control fractions and also for measuring LOHs, 1/10 of the MNCs is removed in each case before and after the screening process (see Example 1). This material is transferred into a reaction vessel containing 1 ml of PBS (0.5% BSA, 100 µg hu-IgG). To this, 50 µl of washed anti-CD45 microbeads are added. The mixture is rotated at 4° C. for 20 min. The reaction vessel is then positioned at a magnetic strip in such a way that the microbeads (bound to CD45 positive MNCs) are pelleted on the vessel wall. Three washings of the bead/cell aggregates result in a pure population of CD45 positive lymphocytes which are then dissolved in Trizol® and used for the isolation of nucleic acids. CD45 isolates of the MNCs prior to the screening process are designated control fraction A, CD45 isolates of the MNCs after the screening process are designated control fraction B.

EXAMPLE 3

DNA Analyses

Genomic DNA is isolated in a conventional manner from the Trizol® solutions obtained in Examples 1 and 2. The DNA is then amplified by PCR using the primers and parameters given below.

1. Analysis of p53, Rb, DCC and APC Alleles:

For each PCR mixture, the following reagents are combined (µl):

| | |
|---|---|
| 10 × buffer | 5 |
| 20 mM dNTP | 0.5 |
| Primer A | 0.5 |
| Primer B | 0.5 |
| TAQ Polymerase + TAQ Start antibody 1:1 | 0.5 |
| H$_2$O | 40 |
| DNA | 3 |

The following temperature profiles are used:

| for APC, Rb and DCC: | | |
|---|---|---|
| 95° C. | 5 min | |
| 94° C. | 30 sec | |
| 53° C. | 30 sec | 35 × |
| 72° C. | 30 sec | |
| 72° C. | 5 min | |
| for p53 | | |
| 95° C. | 5 min | |
| 94° C. | 30 sec | |
| 62° C. | 30 sec | 35 × |
| 72° C. | 30 sec | |
| 72° C. | 5 min | |

The primer pairs used are:

```
p53-LOH:                                        (SEQ ID NO:1)

A: 5'-Fl-Agg gAT ACT ATT CAg CCC CAg gTg (SEQ ID NO:2)
B: 5'-ACT gCC ACT CCT TgC CCC ATT C

APC-LOH                                         (SEQ ID NO:3)

A: 5'-FAM-gTA AgC Agg ACA AgA TgA Cag (SEQ ID NO:4)
B: 5'-gCT ATT CTC TCA ggA TCT Tg

DCC-LOH                                         (SEQ ID NO:5)

A: 5'-HEX-gAT gAC ATT TTC CCT CTA g (SEQ ID NO:6)
B: 5'-gTg gTT ATT gCC Ttg AAA Ag

Rb-LOH                                          (SEQ ID NO:7)

A: 5'-FAM-CTC CTC CCT ACT TAC Ttg T (SEQ ID NO:8)
B: 5'-AAT TAA CAA ggT gTg gTg g
```

All primers are stored at a concentration of 20 pmol/µl. Normal DNA is always used as negative control. All PCR amplicons of the LOH analyses and amplification analyses are measured and evaluated in an ABI-Prism Genescan Genetic Analyzer.

2. Amplification Analysis of erb-B2 and c-myc

A coamplification of erb-B2 (c-myc) versus β-globin is measured.

For each PCR mixture, the following reagents are combined (µl):

|  | c-myc | erb-B2 |
|---|---|---|
| 10 × PCR buffer | 5 | 5 |
| MgCl (25 mM) | 4 | 4 |
| 20 mM dNTP | 0.25 | 0.25 |
| Primer A | 2 | 1.5 |
| Primer B | 2 | 1.5 |
| β-Globin primer A | 0.2 | 0.5 |
| β-Globin primer B | 0.2 | 0.5 |
| (NH₄)₂SO₄ | 7.5 | 7.5 |
| AmpliTaq Gold | 0.4 | 0.4 |
| H₂O | 25.45 | 25.85 |
| DNA | 3 | 3 |

The following temperature profile is used:

| | | |
|---|---|---|
| 95° C. | 10 min | |
| 95° C. | 60 sec | |
| 60° C. | 60 sec | 32 × |
| 72° C. | 60 sec | |
| 72° C. | 3 min | |

The primer pairs used are:

```
erb-B2                                          (SEQ ID NO:9)

A: 5'-HEX-Cgg ATC TTC TgC TgC CgT Cg (SEQ ID NO:10)
B: 5'-CCT Ctg Acg TCC ATC ATC TC c-myc                                           (SEQ ID NO:11)

A: 5'-HEX-CgT ATT CAT gCC Ttg TAT Ttg (SEQ ID NO:12)
B: 5'-CTT CTT CAT CTT CTT gTT CC

Globin                                          (SEQ ID NO:13)

A: 5'-FAM-ACA CAA Ctg TgT TCA CTA Gc (SEQ ID NO:14)
B: 5'-CAA CTT CAT CCA CgT TCA CC
```

All primers are stored at a concentration of 20 pmol/µl. Normal DNA is always used as negative control and 5-fold amplified (erb-B2/c-myc) DNA is used as positive control. All PCR amplicons of the LOH analyses and amplification analyses are measured and evaluated in an ABI-Prism Genescan Genetic Analyzer.

EXAMPLE 4

Clinical Application 14 patients having different carcinomas, one patient having a malignant melanoma, six control donors and one "normal donor" whose result from a preliminary examination was remarkable were studied. Analyses of tumor-specific and tumor-associated PNAs and also genomic analyses on allele imbalance (LOH) of the genes p53, Rb, APC and DCC, and amplification analyses of the c-myc and erb-B2 oncogenes were carried out.

According to Example 1, the control fraction, screen flow-through and screen residue were obtained from the blood of each patient. According to Example 2, CD45 positive controls were isolated as wild-type control from the control fraction and the screen flow-through (fractions A and B). The analyses mentioned above were carried out on CD45 positive cells of the control fraction (A; reference), on CD45 positive cells of the screen flow-through (fraction B) and on cells of the screen residue (fraction C).

For the genomic analyses for patients and for control donors, the relative allele differences with respect to the CD45 control fraction A (reference) were determined. The cut-off of the LOH analyses with respect to the control was set to a value of ≦0.5, i.e. a positive result has at least a difference of 50%. The amplification analyses had a cut-off of 2.0.

For five of the 15 patients studied having an established carcinoma and melanoma, it was shown that it was possible to isolate disseminated cancer cells from peripheral blood using the method of the invention. This was also possible for one of the control donors whose preliminary examination result (expression of CEA, CK20 and MUC1 RNAs) had indicated disseminated cancer cells.

EXAMPLE 5

Characterizing the Biological State of Disseminated Tumor Cells

A blood sample was taken from a 53-year old patient having a breast carcinoma (pT2pNlM0, G3) which had been diagnosed 16 months earlier and had been treated (6xCMF, radiation, tamoxifen). Disseminated tumor cells were isolated according to Example 2. These had an LOH of the p53 gene, a mutation of the p53 gene and an amplification of c-erbB-2. The quantitative and GAPDH-normalized analysis of cyclin expression gave the following result:

| Cyclin D: | 2.5 |
|---|---|
| Cyclin E: | 0 |
| Cyclin B: | 0 |

The exclusive expression of cyclin D indicates a G0/1 phase. None of the isolated cells was in a mitotic state. The isolated tumor cells were unable to proliferate.

A blood sample was taken from a 64-year old male patient having a colon carcinoma (Dukes C) which had been diagnosed 6 months earlier and had been treated (5-FU). Disseminated tumor cells were isolated according to Example 2. These had an LOH of the DCC gene, an LOH of the E-cadherin gene and an amplification of c-myc. The quantitative and GAPDH-normalized analysis of cyclin expression gave the following result:

| Cyclin D: | 0.7 |
|---|---|
| Cyclin E: | 4.3 |
| Cyclin B: | 10.3 |

The expression of all three cyclins indicates a proliferative state of the isolated tumor cells.

---

The invention claimed is:

1. A method for isolating disseminated tumor cells from a cell-containing body fluid, consisting essentially of passing a cell-containing body fluid or part thereof that comprises a disseminated tumor cell through a screen having a mesh or pore width of about 15 to 30 μm to separate non-cancer cells from disseminated tumor cells, wherein the disseminated tumor cells are retained on the screen wherein the body fluid is selected from the group consisting of blood and bone marrow, wherein the disseminated tumor cells are not modified prior to screening by labeling, by attaching particles, by triggering aggregation, by triggering cluster formation, with antibodies, enzymes, lectins, other ligands, other receptors or cross linking agents or by fixing.

2. A method for isolating disseminated tumor cells from a cell-containing body fluid, consisting essentially of separating cellular components from non-cellular components in a body fluid that comprises a disseminated tumor cell to obtain a cell-containing fraction; resuspending the cell-containing fraction in a suspension medium; and passing the resuspended cell-containing fraction through a screen having a mesh or pore width of about 15 to 30 μm to separate non-cancer cells from disseminated tumor cells, wherein the disseminated tumor cells are retained on the screen, and wherein the body fluid is selected from the group consisting of blood and bone marrow, wherein the disseminated tumor cells are not modified prior to screening by labeling, by attaching particles, by triggering aggregation, by triggering cluster formation, with antibodies, enzymes, lectins, other ligands, other receptors or cross linking agents or by fixing.

* * * * *